US010405895B2

(12) United States Patent
Omar-Pasha

(10) Patent No.: US 10,405,895 B2
(45) Date of Patent: Sep. 10, 2019

(54) DEVICE FOR SUPPORTING A SPINAL COLUMN AND FOR SPREADING TWO ADJACENT RIBS

(71) Applicants: Omar Omar-Pasha, Lohmar (DE); Gert Stephanus Becker, Pretoria (ZA); Paul Carel Hubertus De Joode, Rhenen (NL)

(72) Inventor: Omar Omar-Pasha, Lohmar (DE)

(*) Notice: Subject to any disclaimer, the term of this patent is extended or adjusted under 35 U.S.C. 154(b) by 0 days.

(21) Appl. No.: 15/562,119

(22) PCT Filed: Mar. 24, 2016

(86) PCT No.: PCT/EP2016/056524
§ 371 (c)(1),
(2) Date: Sep. 27, 2017

(87) PCT Pub. No.: WO2016/156189
PCT Pub. Date: Oct. 6, 2016

(65) Prior Publication Data
US 2018/0078288 A1    Mar. 22, 2018

(30) Foreign Application Priority Data
Mar. 27, 2015   (DE) .................. 10 2015 104 784

(51) Int. Cl.
*A61B 17/70* (2006.01)
(52) U.S. Cl.
CPC ........ *A61B 17/7065* (2013.01); *A61B 17/707* (2013.01); *A61B 17/7067* (2013.01)

(58) Field of Classification Search
CPC ............ A61B 17/7065; A61B 17/7067; A61B 17/707
(Continued)

(56) References Cited

U.S. PATENT DOCUMENTS

| 8,425,559 B2* | 4/2013 | Tebbe | A61B 17/7062 606/248 |
| 8,672,976 B2* | 3/2014 | Kilpela | A61B 17/70 606/249 |

(Continued)

FOREIGN PATENT DOCUMENTS

WO    WO-2013029188 A1 *  3/2013  ......... A61B 17/6466

*Primary Examiner* — Pedro Philogene
*Assistant Examiner* — David C Comstock
(74) *Attorney, Agent, or Firm* — Cohen & Grigsby, P.C.

(57) ABSTRACT

The invention refers to a device 1 for supporting a spinal column in the region of the transverse or spinous processions of two adjacent vertebrae and/or for spreading two adjacent ribs, comprising at least a first body 2 and a second body 3, each body having a receptacle 4 for a transverse or spinous process of a vertebra or for a rib; and a rotational joint 12 between the first body 2 and the second body 3, such that the first body 2 and the second body 3 are rotatable relative to one another about a common axis of rotation X, wherein the distance between the receptacles of the first body 2 and the second body 3 can be adjusted by means of the rotational movement of the first body 2 relative to the second body 3, which is characterized in that the receptacles 4 of the first body 2 and the second body 3 are designed such that the transverse or spinous processes of adjacent vertebrae or adjacent ribs can be received therein at least in a rotational angle of 0° to 180°, preferably 0° to 270°, of the first body 2 to the second body 3.

19 Claims, 6 Drawing Sheets

(58) Field of Classification Search
USPC ........ 606/248, 249; 623/17.11, 17.15, 17.16, 623/23.47
See application file for complete search history.

(56) References Cited

U.S. PATENT DOCUMENTS

| | | | | |
|---|---|---|---|---|
| 2009/0149886 A1* | 6/2009 | Zentes | ................ | A61B 17/7065 606/249 |
| 2009/0292314 A1* | 11/2009 | Mangione | .......... | A61B 17/7062 606/249 |
| 2011/0313457 A1* | 12/2011 | Reglos | ................ | A61B 17/3468 606/249 |
| 2013/0310937 A1* | 11/2013 | Pimenta | ................ | A61F 2/4425 623/17.15 |
| 2014/0018920 A1* | 1/2014 | Mouw | ....................... | A61F 2/44 623/17.11 |

* cited by examiner

DEVICE FOR SUPPORTING A SPINAL COLUMN AND FOR SPREADING TWO ADJACENT RIBS

BACKGROUND OF THE INVENTION

Field of the Invention

The invention relates to a device for supporting a spinal column in the region of the transverse processes or spinous processes of two adjacent vertebrae and/or for spreading two adjacent ribs.

A constriction of a vertebral canal (spinal canal stenosis) may occur due to bony excrescences on the vertebral column (spondylophytes), thickening of the ligaments, arthrosis of the small vertebral arches (spondyl arthrosis) or warping of the spine (scoliosis). As a result of a progressive narrowing of the spinal canal, the nerve structures emerging through the spinal canal become irritated.

Spinal canal stenoses can occur both centrally and laterally.

US 2007/0233098 A1 discloses height-adjustable devices which can be inserted between the spinous processes of two adjacent vertebrae in order to treat a central stenosis. Further, devices are disclosed which are adaptable to an insert between the transverse processes of two adjacent vertebrae. A disadvantage of the devices known from US 2007/0233098 A1 is that they are relatively large and have to be inserted or implanted by a larger surgery. Moreover, the stability of the devices can be improved in particular when setting a large height. It is disadvantageous that the parts of the device are interleaved. This requires high precision in the manufacture of the parts, resulting in increased production costs. Moreover, long-term use and a long-term load can lead to wedging. This can occur, in particular, in the case of imprecisely manufactured parts, so that at a later stage no adjustment of the device is possible any more.

Discussion of the Prior Art

In the case of lateral stenoses which constrict the intervertebral foramina, which leads to compression and irritation of the spinal nerves, it is known from the prior art to expand the intervertebral tracts surgically. In order to keep the intervertebral discs open, the affected vertebrae must usually be stiffened (spondylodesis). However, this has the disadvantage that the instability is often displaced to the neighboring vertebrae.

DE 10 2011 117 724 A1 discloses a device for supporting a spinal column in the region of the transverse processes of two adjacent vertebrae. The device has two bodies with receptacles for receiving the transverse processes, and a support device by means of which the bodies can be moved relative to one another. In this case, the first body is hollow, so that the second body can be arranged in the first body. By means of the support device, the second body can be moved out of the first body in order to support a spinal column. It is disadvantageous that a high precision is required in the manufacture of the parts since, on the one hand, a body has to be arranged inside the second body and, on the other hand, the cavity has to be produced in such a precise manner that when the one body is pushed out of the other on a predefined path, which is defined by the cavity, in such a way that an engagement of transverse processes in the receptacles is possible. Moreover, this device is suitable only for the application for supporting a spinal column in the region of transverse extensions.

US 2009/0248079 A1 discloses a device for supporting a spinal column in the region of the spinous processes of two adjacent vertebrae. The device comprises two hook-shaped elements, wherein one respective spinous process of adjacent vertebrae is being arranged within the recess of a hook-shaped element. In order to adjust and fix a certain distance between the hook-shaped elements, the hook-shaped elements are arranged on an elongated guide element, for example a rod, and can be fixed relative to this guide element. According to an alternative embodiment, the hook-shaped elements are connected to one another at a pivot point, which allows a relative rotational movement between the two hook-shaped elements. During implantation, the hook-shaped elements are rotated relative to one another until the spinous processes of adjacent vertebrae are arranged within the hook-shaped elements and are thereby supported. A disadvantage of this embodiment is, however, that, owing to the hook-shaped configuration, the elements can only accommodate the spinous processes of adjacent vertebrae in a relatively small range, and thus the distance between the hook-shaped elements during supporting the adjacent vertebrae in the area of the spinous processes can only be set in a very restricted range.

US 2011/0238114 A1 disclosed another device for supporting a spinal column in the region of the spinous processes, comprising two hook-shaped elements for receiving the spinous processes of adjacent vertebrae. The hook-shaped elements are connected to each other by means of a connecting element, the connecting element being at least partially flexible or collapsible and capable of being stiffened in an implanted state. During the implantation of the device, the device is bent or folded in the region of the flexible or collapsible connecting element, as a result of which the size of the device, in particular its length, is reduced. After insertion of the device into the human or animal body, the device is bent or folded back into the original shape until the spinous processes of adjacent vertebrae are received in the hook-shaped elements of the device. Finally, the connecting element is stiffened in the flexible or collapsible area so that the spinous processes of adjacent vertebrae are supported. A disadvantage of this device is the design of the connecting element with a flexible or collapsible area and the possibility of stiffening the area after successful implantation which is necessary in this respect.

Furthermore, devices for spreading ribs are known from the state of the art which, however, cannot be used for supporting a spinal column in the region of the transverse or spinous processes.

SUMMARY OF THE INVENTION

Based on this state of the art, the invention is based on the object of providing a device for supporting a spinal column in the region of the transverse or spinous processes and/or for spreading two adjacent ribs which can be inserted into the patient through a minimally invasive procedure, wherein the device can in particular be simply adapted in the implanted state by means of a further minimally invasive surgery and is also improved in terms of stability.

This object is solved by a device for supporting a vertebral column in the region of the transverse or spinous processes of two adjacent vertebrae and/or for spreading two adjacent ribs, comprising at least a first body and a second body, each having a receptacle for a transverse or spinous process of a vertebra or of a rib; and a rotational joint between the first body and the second body, such that the first body and the second body are rotatable relative to one another about a common axis of rotation, wherein the distance between the receptacles of the first body and the second body can be adjusted by means of the rotational movement of the first body relative to the second body, which is characterized in that the receptacles of the first body and of the second body are designed such that the transverse or spinous processes of adjacent vertebrae or adjacent ribs can be received therein at least in a rotational angle of 0° to 270° of the first body to the second body. The device has the advantage that the intervertebral foramina is dynamically kept open during a lateral stenosis without fixing the vertebrae relative to each other. By means of a double-sided application of the device according to the invention, a central spinal canal stenosis can also be dynamically kept open. The intervertebral foramina is kept open dynamically because the device is inserted between the transverse processes and is therefore not far from the pivot point of the vertebrae. In addition, it is possible to use the device between the spinous processes of adjacent vertebrae and thus also to dynamically open a central spinal canal stenosis. In the implanted state of the device, the direction of movement of the transverse or spinous processes received in the receptacles of the device is limited only in one direction, namely toward one another. However, movement of the transverse or spinous processes into the counter-direction is possible. There is thus no fixation, but merely a support. The advantage of this dynamic support is that only an unwanted movement direction, which supports the healing process, is prevented with the device according to the invention. However, a complete immobility of the vertebrae is avoided.

The device according to the invention is also suitable as a so-called rib spreader, by means of which adjacent ribs can be spread apart. In the case of rib fractures, dynamic manipulation or stabilization can thus take place.

In order to use the device according to the invention in a patient, it is set to a first operating state. In this first operating state, the device can be inserted or implanted by a minimally invasive procedure in a patient. The longitudinal extent is advantageously greater than the transverse extent of the device, the transverse extent being perpendicular to the longitudinal extent. When the device is inserted into a patient, it can be placed in a second operating state. In this second operating state, transverse or spinous processes of adjacent vertebrae or adjacent ribs engage in the receptacles of the first and second bodies of the device. This is achieved by the fact that the transverse expansion of the device increases as long as the corresponding transverse or spinous processes or ribs engage in the receptacles of the first and second bodies. Accordingly, for example, the longitudinal expansion of the device in the first operating state is approximately twice as great or greater than the transverse extent of the device, and in the second operating state the longitudinal expansion is smaller. The distance between the receptacles of the first body and the second body is adjusted by a relative rotational movement of the first body to the second body. According to the invention, the receptacles of the first body and/or second body are designed in such a way that the transverse or spinous processes of adjacent vertebrae or adjacent ribs are arranged therein at least at an angle of rotation of 0° to 180°, preferably 0° to 270°, of the first body relative to the second body. Thus, the distance between the receptacles of the first body and the second body can be adjusted relative to one another in as wide a range as possible.

The rotational joint of the device according to the invention allows a relative rotational movement between the first body and the second body and at the same time prevents all other types of relative movements between the first body and the second body.

A further advantage of the device is that, particularly in the second operating state, a high stability is provided. Because the first and second bodies form a pivot, the distance between the receptacles of the first body and the body is variable. The first body and the second body are substantially similar. This allows a particularly stable construction to be ensured. Auxiliary elements such as a supporting device connecting the two bodies can be dispensed. Furthermore, this has the advantage that the construction is kept simple, whereby the production costs can be optimized. A further advantage of the rotational joint is that no wedging between the two bodies of the device is possible. The first body and the second body are connected to each other via the rotational joint such that the movement about a common axis of rotation in one direction is possible and, accordingly, the rotational joint has one degree of freedom. By means of the rotational joint, a wedging known from the prior art can be effectively avoided due to freely movable bodies of such devices.

According to a particularly preferred variant of the invention, the receptacle of the first body and/or of the second body has a concave surface. The concave surface is parallel to the direction of rotation of the first body relative to the second body. All the devices known from the prior art for supporting a spinal column have convex receptacles for the transverse processes or spinous processes, wherein the corresponding transverse processes or spinous processes being arranged in the recess of the convex receptacle. In contrast, the receptacle according to the invention preferably has a concave shape in the direction of rotation so that the transverse process, the spinous process or the rib can rest on the outwardly curved surface, independent of the relative rotational movement of the first body to the second body, and the resulting rotational movement of the receptacles to each other. According to an advantageous embodiment of the invention, the concave surface of the receptacle of the first body and/or of the second body covers at least a quarter circle, preferably a semicircle.

In a preferred embodiment, the axis of rotation is arranged outside the center of gravity of the first body or the second body. The axis of rotation runs at right angles to the longitudinal extent of the first body and the second body and is arranged in the terminal third of the first body and the second body, respectively. Around the common axis of rotation, the first and second bodies are rotatable relative to one another such that they form a rotational joint so that the receptacles of the first and second bodies can exert a shearing action for supporting the spine and/or for spreading ribs.

In a variant of the invention, the axis of rotation of the device is arranged at the opposite end of the respective receptacle of the first body and/or of the second body.

An embodiment of the invention further comprises a control device for controlling the relative rotational movement between the first body and the second body. By means of the control device, the device can be adapted to the distance between the transverse processes or the spinous processes of the adjacent vertebrae and can also be set such that the intervertebral foramina is opened. In addition, by means of the control device, the device can be adapted to the spacing between successive or adjacent ribs for spreading, or the distance between the receptacles of the device can be changed such that spreading of ribs is possible.

In a further embodiment of the invention, the control device is designed in one piece with the first body or the second body. Through the one-part design, the design can be simplified, resulting in simpler manufacture and lower production costs. In addition, the device is more stable against the forces to be applied when changing the distance between the receptacles of the device.

In a preferred embodiment of the invention, the rotational joint is a lockable rotational joint so that different angles between the first and second bodies can be adjusted and ascertained. The rotational joint can, for example, be fixed in a position by means of a locking device. For the support of a spinal column and/or the spreading of two adjacent ribs, the desired distance between the receptacles of the first body and the second body can be altered and adjusted and locked/blocked by the surgeon.

One embodiment of the invention is characterized in that the angle which can be adjusted by the rotational joint is 0° to about 270°, preferably 0° to about 180°. The maximum distance between the receptacles of the first and second bodies is set at an angle of approximately 180° on the device according to the invention. At an angle of about 0°, the distance between the receptacles of the first and the second body, on the other hand, is minimal. The angle of 0° can in particular be selected for the minimally invasive insertion during the implantation of the device into a patient since in this case the dimensions of the device are minimal for a minimally invasive surgery.

A further embodiment of the invention is characterized in that the angle is adjusted in predefined stages. The device according to the invention can be adapted to changing conditions. The advantage of predefined stages is that the adaptation is easier to carry out for an adjusting user or surgeon, since the adjustment of the angle simultaneously locks this setting.

A further embodiment of the invention is characterized in that the first body has a bulge and the second body has at least one, preferably several, indentations so that the bulge engages in at least one indentation for adjusting the angle between the first body and the second body. The bulge can be designed in the shape of a nose and the indentation corresponding to the bulge. The bulge can be moved in and out of the indentation. This advantageously takes place via the control device for controlling the relative movement between the first body and the second body. The bulge forms a locking together with the indentation. The use of such a locking mechanism has the advantage that the device according to the invention does not move during a load.

Advantageously, the first body and the second body each have a bulge and at least one indentation, wherein in each case the bulge of the one body engages in the indentation of the other body. The locking of the two bodies relative to one another when setting an angle develops an improved support in this way and the device according to the invention can withstand higher loads. The control device is operable through an opening at the distal end of the device. This ensures that the device can also be actuated after implantation. The term "distal" within the scope of the present disclosure means the end of the device facing the user (surgeon) and the indication "proximal" within the scope of the present disclosure means the end of the device facing away from the user (surgeon).

A further embodiment of the invention provides that the rotational joint is realized via a type of gear transmission. In this case, the first body of the device has a toothed wheel or gearwheel-like bulges which are arranged centered along or around the axis of rotation. The second body has corresponding elements, so that an engagement of the shapings or teeth according to a toothed wheel principle is made possible. The teeth of the toothed wheels need not be arranged completely along a circle, but can only have a part of the teeth, so that there is a limitation of the rotation between the first body and the second body of the device. Locking in the use of such a gear principle can, for example, be realized via a pin, which engages in a tooth.

In a preferred embodiment of the invention, the distance in a first operating state between the receptacles of the device is minimal and in a second operating state in which the transverse or spinous processes of adjacent vertebrae or a respective rib engage in the receptacles of the first and second bodies the distance between the receptacles is larger. The space requirement of the device according to the invention is minimized in that the size of the device during implantation is as small as possible so that the device can be inserted or implanted with a minimally invasive surgery in a patient. When the device is implanted, the user (surgeon) can increase the distance between the receptacles between the first and the second body so that transverse or spinous processes of adjacent vertebrae or ribs respectively engage in the receptacles and support the spinal column and/or spread the ribs can be carried out.

A further embodiment of the invention is characterized in that the receptacle of the first body and/or of the second body has raised edge regions which prevent slipping of the receptacle from a transverse process or spinous process or from a rib. The receptacle thus has a substantially U-shaped cross-section transverse to the direction of rotation between the first body and the second body.

The receptacles therefore have two limbs each having a free end and a limb connecting the limbs with the free end. The connecting limb forms a stop surface for engaging transverse or spinous processes or for ribs. The legs with the free end at least partially encompass the transverse or spinous processes or ribs engaging in the receptacles and prevent them from being moved laterally out of the receptacles. They thus form a lateral abutment surface and ensure a secure lateral support for the transverse or spinous processes or ribs engaging in the receptacles. In particular, the forces occurring in the support of a spinal column and/or spreading of ribs can be applied by means of the essentially U-shaped receptacles of the device. As a result, slipping off of the device according to the invention can be avoided. At the same time, the receptacles in the direction of rotation have a concave surface according to the invention.

Advantageously, the receptacles for the transverse or spinous processes of a vertebra or ribs of the first body or of the second body have a padding for the transverse or spinous processes or ribs to be accommodated.

In one embodiment of the invention, the receptacle of the first and/or the second body has a bore for fixing a received transverse or spinous process or a received rib. Accordingly, an additional fixing of the received transverse or spinous processes or ribs in the receptacles can take place, for example, by means of a screwed connection, a clamp or the like. Advantageously, the bore is arranged in one of the limbs with the free end of the essentially U-shaped receptacle.

According to a suitable variant of the invention, the dimensions of the device according to the invention during insertion into the human or animal body do not exceed 2.5×1.5×1.5 cm, preferably not 2.1×1.1×1.1 cm, before a relative rotational movement between the first body and the second body.

BRIEF DESCRIPTION OF THE DRAWINGS

Further details, features and advantages of the invention are explained in more detail below with reference to the exemplary embodiments shown in the figures. In this connection.

DESCRIPTION OF A PRESENTLY PREFERRED EMBODIMENT

Figure 1:
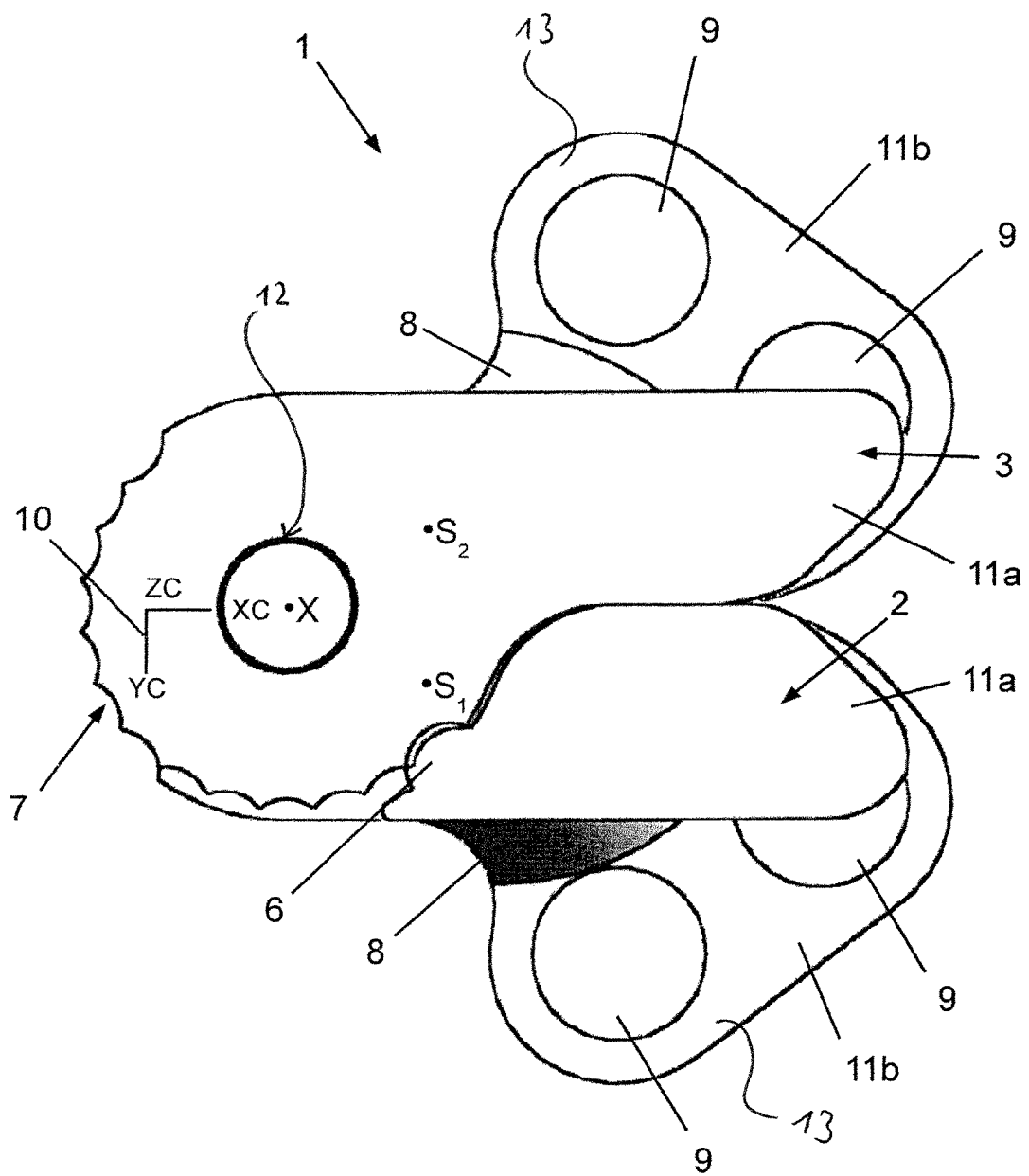
FIG. 1 shows a representation of a device according to the invention in a side view from the left.

FIG. 1 shows a device 1 for supporting a spinal column in the region of the transverse or spinous processes of two adjacent vertebrae and/or for spreading two adjacent ribs. The device 1 comprises at least a first body 2 and a second body 3 which each have a receptacle 4 for a transverse or spinous process of a vertebra or for a rib. The first body 2 and the second body 3 can be moved relative to one another so that in each case a transverse or spinous procession of adjacent vertebrae or a respective rib engages in the receptacles 4 of the first body 2 or of the second body 3, respectively. For this purpose, the device 1 has a rotational joint 12 between the first body 2 and the second body 3, so that the first body 2 and the second body 3 can be rotated relative to one another about a common axis of rotation X, as a result of the rotary movement of the first body 2 relative to the second body 3, the distance between the receptacles 4 of the first body 2 and the second body 3 can be adjusted. The invention is characterized in particular by the fact that the receptacles 4 of the first body 2 and of the second body 3 are designed in such that the transverse or spinous processes of adjacent vertebrae or adjacent ribs can be received therein at least in a rotational angle of 0° to 180°, preferably 0° to 270°, of the first body 2 to the second body 3.

Figure 4:
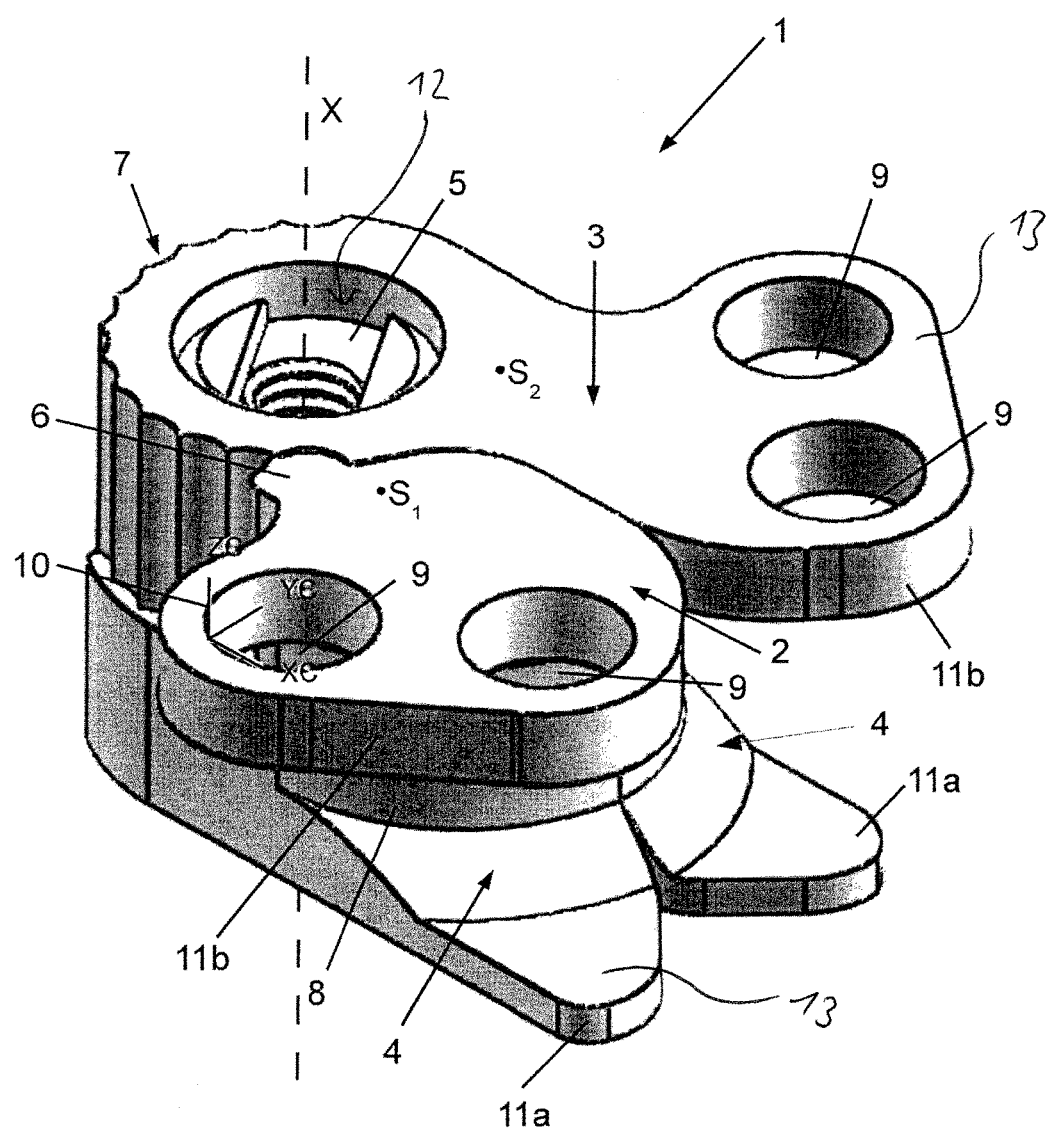
FIG. 4 is a perspective view of a device according to the invention.
Figure 5:
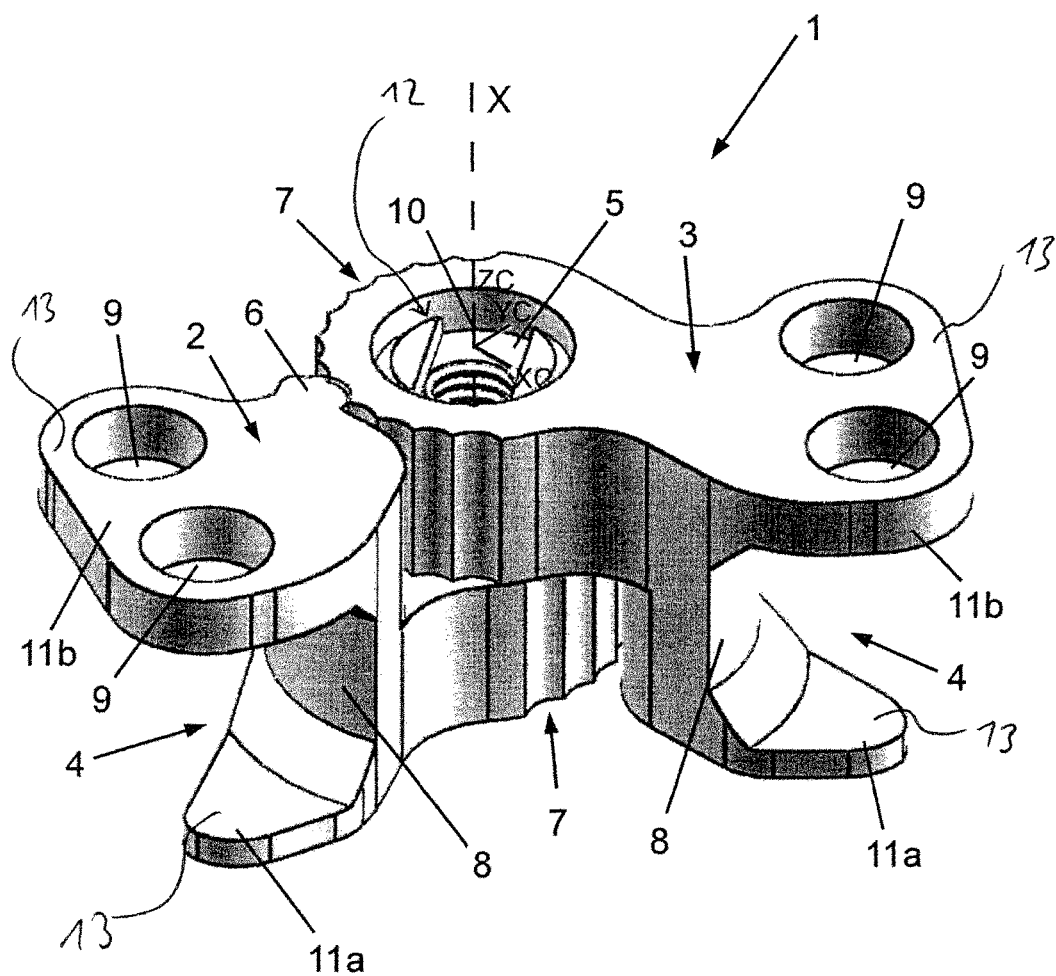
FIG. 5 shows a perspective illustration of the device according to FIG. 4 after a relative movement and FIG. 6 is a further perspective view of the device according to FIG. 5.
Figure 6:
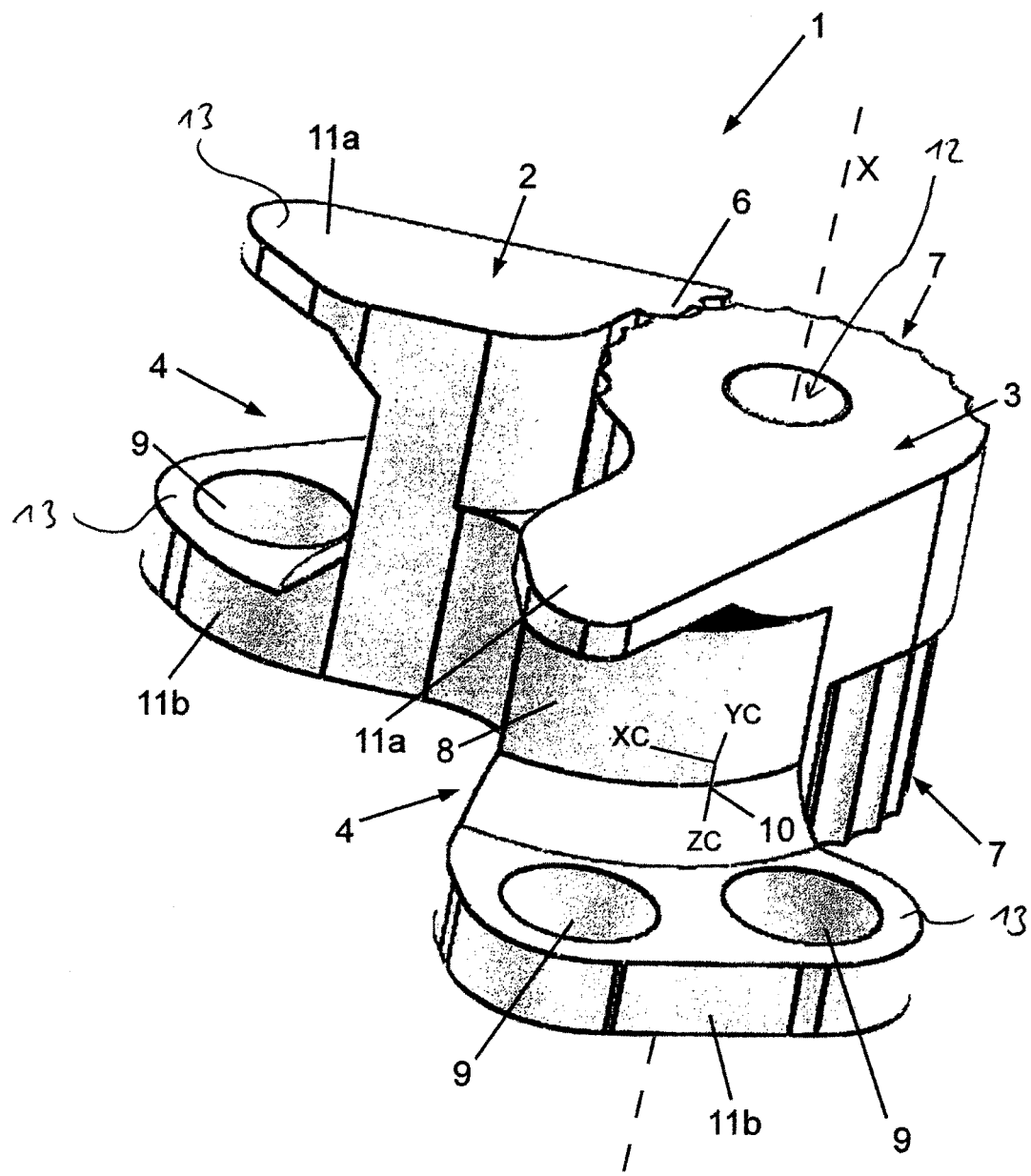

The receptacle 4 of the first body 2 and of the second body 3 has a concave surface in the direction of the rotary movement of the rotational joint, as can be seen, for example, in FIGS. 4 to 6. The concave surface of the receptacle 4 covers at least a quarter circle, preferably a semicircle.

The device 1 furthermore comprises in each limb with the free end 11b of the first body 2 and the second body 3 two bores 9. At its end, the second body 3 has a plurality of indentations 7, which are designed to receive a correspondingly shaped bulge 6 of the first body 2. The bulge 6 can in each case be moved into and out of one of the indentations 7. In this way, different angles can be set between the first body 2 and the second body 3 via the rotational joint 12. As a result of the engagement of the bulge 6 in one of the indentations 7, the rotational joint is also fixed in the corresponding position. The adjustment of the angle of the rotational joint 12 takes place in predefined stages.

The axis of rotation X is arranged outside the centers of gravity S1, S2 of the first body 2 or of the second body 3 and is located centered on the opposite end of the receptacles 4 on the respective first or second body 2, 3 of the device 1.

In FIG. 1, the device 1 according to the invention is shown in a first operating state, in which the distance between the receptacles 4 of the device 1 is minimal. The same applies to the angle set via the rotational joint 12, which is also minimal and is 0° in the present case.

The device 1 has a further limb 11a with the exposed end 11a as an additional component of the receptacles 4 on the first and second bodies 2, 3, respectively, which form a substantially U-shaped receptacle 4 together with the limbs with the end 11b. The U-shape is thereby formed transversely to the direction of rotation of the rotational joint 12.

In FIG. 1, a coordinate system 10 is also shown. This shows the orientation of the three axes XC, YC and ZC lying in the space, which are respectively present in FIGS. 1 to 6 and in each case illustrate the view for the observer or the correspondingly altered rotation of the device 1.

Figure 2:
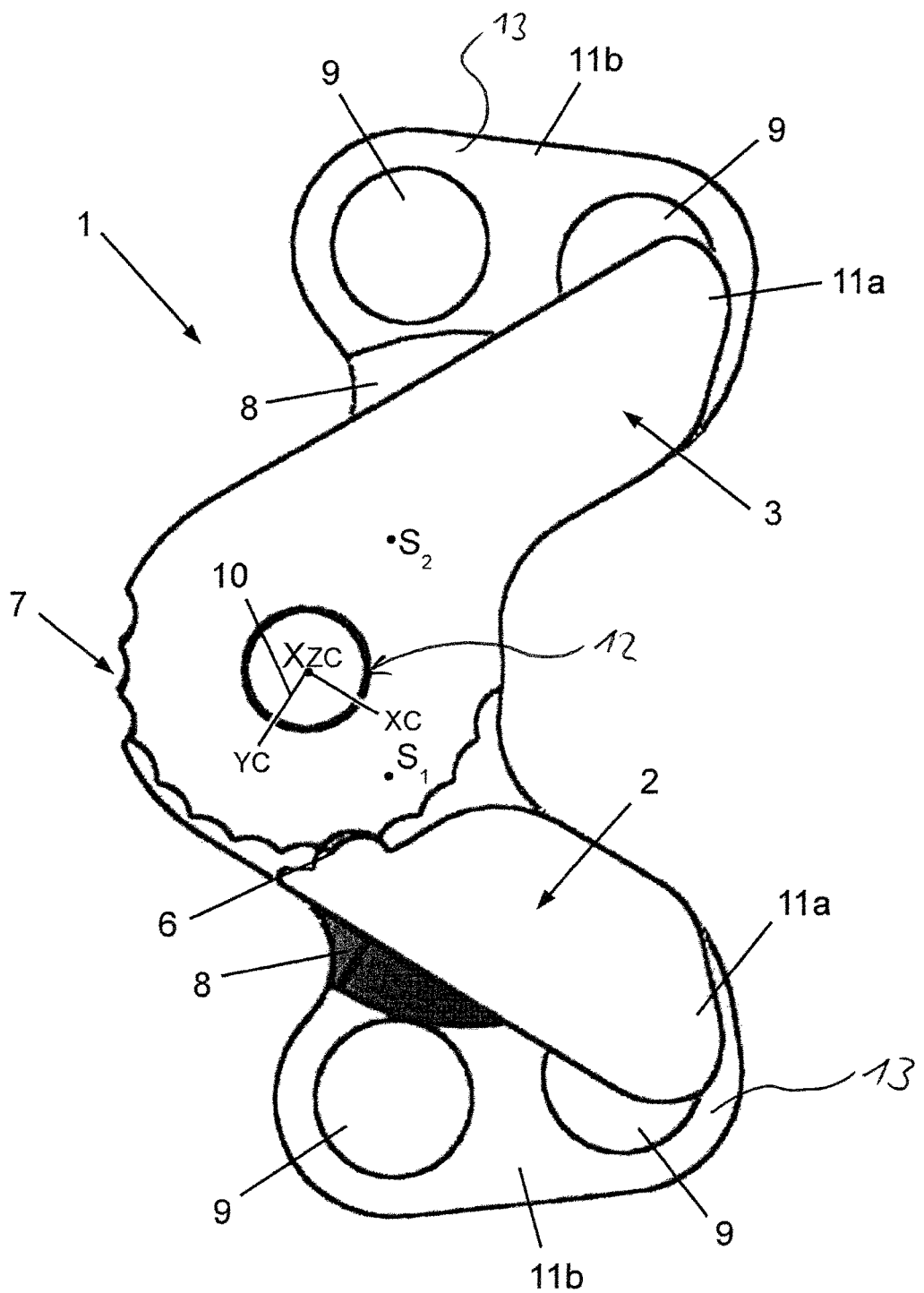
FIG. 2 shows a representation of the device according to FIG. 1 after a relative movement.

FIG. 2 shows a representation of the device 1 according to FIG. 1 in a second operating state after a relative movement between the first body 2 and the second body 3 by a rotation of the two bodies 2, 3 relative to one another about the common axis of rotation X. In the second operating state, the distance between the receptacles 4 is increased in comparison with the illustration according to FIG. 1.

The angle set via the rotational joint 12 is present approximately 130°. The distance of the receptacle 4 is significantly changed or enlarged compared to the representation according to FIG. 1.

The first body 2 and the second body 3 are moved relative to each other until transverse or spinous processes to be supported or ribs to be spread are arranged in the receptacles 4 of the first body 2 and of the second body 3. The first body 2 and the second body 3 can be moved relative to each other until the desired distance is reached between the transverse or spinous processes of the vertebrae or the ribs to be spread. After adjusting the desired distance, the first body 2 and the second body 3 are supported relative to each other, so that the desired spacing between the vertebrae and ribs cannot be undercut. In order to prevent an adjustment of the device 1 according to the invention, the engagement of the bulge 6 into one of the indentations 7 causes a locking and thus a fixing of the rotational joint 12 formed by the two bodies 2, 3. The device 1 thus remains in the second operating state after implantation into a patient. However, the distance of the receptacles 4 of the device 1 according to the invention is variable in the implanted state in the patient by means of a minimally invasive surgery.

According to an advantageous embodiment of the invention, the receptacles 4 of the first body 2 or of the second body 3 have a padding for transverse or spinous processes of vertebrae or ribs.

Figure 3:
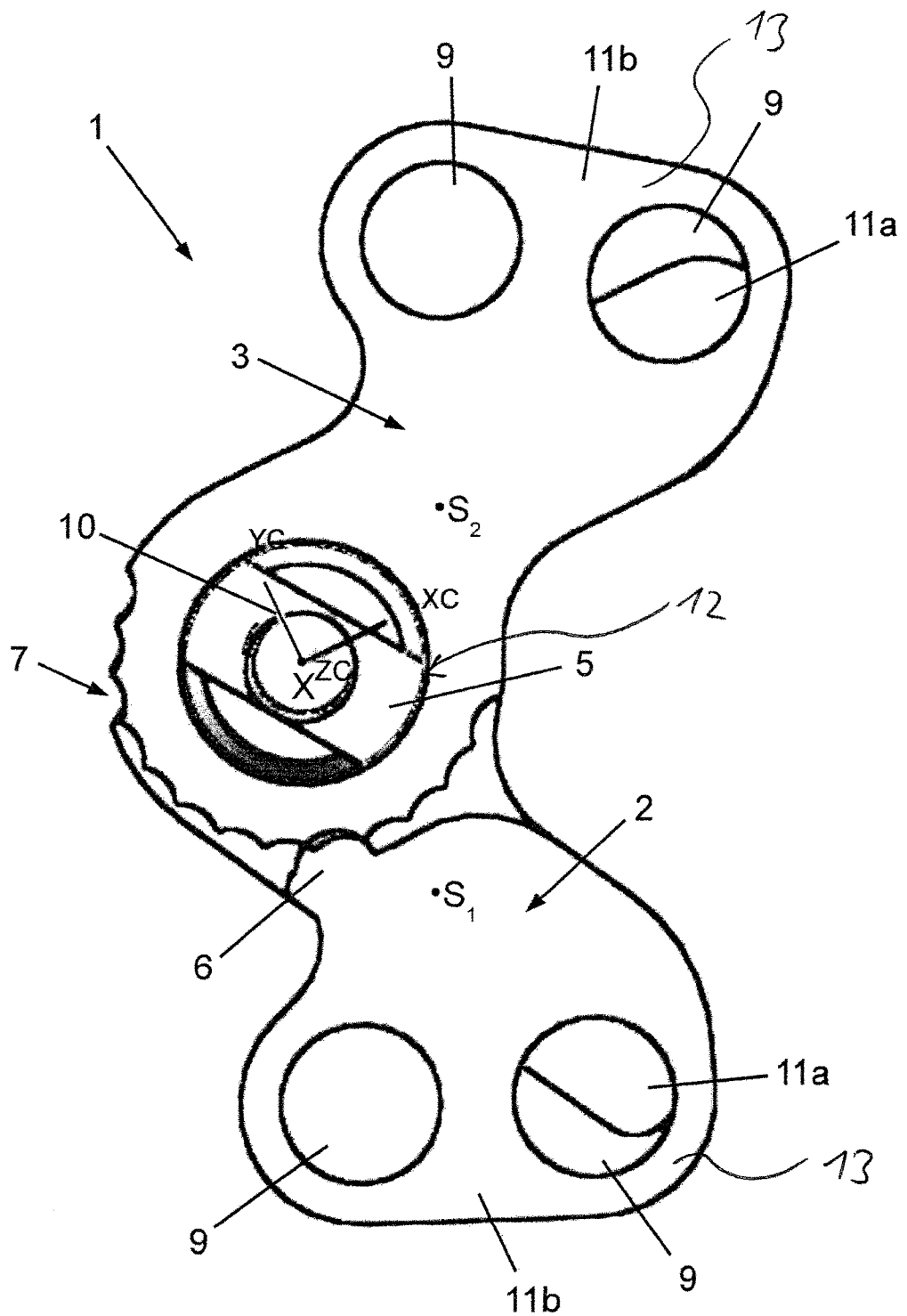
FIG. 3 shows a representation of the device according to FIG. 2 in a side view from the right.

FIG. 3 shows the device 1 according to FIG. 2 in a side view from the right. 2. In contrast to FIG. 2 the control device 5 can now be seen. In this case, the control device 5 is designed in one piece with the second body 3 so that a relative movement of the first body 2 relative to the second body 3 can take place by a rotation of the control device 5. For this purpose, the control device 5 has an indentation for the engagement of a tool, by means of which, for example, a change in the distance between the receptacles 4 of the first or the second body 2, 3 can be performed by a user (surgeon) via a minimally-invasive surgery. This ensures that, for supporting a spinal column, the vertebral canal does not fall below a certain diameter between a first vertebra and a second vertebra. When spreading ribs it is thereby achieved that the distance between two adjacent ribs or two successive ribs on one side of a breast basket is so large that a corresponding surgery can be performed by a user (surgeon).

In combination with FIG. 2 it is clear in FIG. 3 that both the first body 2 and the second body 3 have indentations 7 as well as a respectively one bulge 6. The bulge 6 of the first body 2 engages in at least one of the indentations 7 of the second body 3 and the bulge 6 of the second body 3 in indentations 7 of the first body 2. The force of the locking of the rotational joint (arresting) between the first body 2 and the second body 3 is thus strengthened.

In FIG. 4 a perspective view of a device 1 according to the invention is shown. The coordinate system 10 shows the orientation of the perspective representation with reference to the further figures. The device 1 is shown in a first operating state in which the distance between the receptacles 4 of the first body 2 or of the second body 3 is minimal. It can be seen from FIG. 4 that the receptacles 4 of the first body and the second body 3 are formed so as to have a substantially concave abutment surface 8. The abutment surface 8 of the receptacle 4 of the first body 2 or of the second body 3 has a shape substantially corresponding to the shape of the transverse or spinous processions of vertebrae or ribs. This enhances the support of the device 1 so that during a movement of the spinal column during the support of the spinal column or during a movement of two ribs towards one another during the spreading of ribs the device 1 will not dislocate.

Further it can be seen from FIG. 4 that the receptacles 4 of the first body 2 and of the second body 3 are designed essentially U-shaped transversely to the direction of rotation of the rotational joint. The receptacle 4 of the first body 2 or of the second body 3 thus has raised edge regions 13, which prevent slipping of the receptacle 4 from a transverse process or spinous process or from a rib. In this case, the stop surface 8 forms a connecting limb between the limbs with the free end 11a, 11b, respectively, as a component of the first body 2 and of the second body 3.

The control device 5 shows a slot-shaped indentation, by means of which an inspector (surgeon) with a correspondingly designed tool can engage the indentation of the control device 5 and can change the distance between the receptacles 4 of the device 1. By a rotary movement of the control device 5, the bulges 6 of the device 1 are each moved out of an indentation 7 and moved into a further indentation 7. FIG. 5 shows a perspective view of the device according to FIG. 4 after a relative movement of the first body 2 and the second body 3 relative to one another.

From FIG. 5 it can be seen that the first body 2 and the second body 3 each have a plurality of indentations 7 for the engagement of the bulge 6 of the first and second bodies 2, 3, respectively. Furthermore, it can be seen that the width of the receptacles 4 is approximately twice as wide as the end of the first body 2 or the second body 3 facing away from the receptacles. As a result, forces absorbed by the receptacles 4 are optimally distributed to the rotational joint 12 and the device 1 is thus particularly stable.

FIG. 6 shows a further perspective view of the device according to FIG. 5.

Advantageously, the dimensions of the device 1 during insertion into the human or animal body do not exceed 2.1×1.1×1.1 cm before a relative rotational movement between the first body 2 and the second body 3.

The exemplary embodiments illustrated and described in the figures of the drawings are merely illustrative for the invention and are not intended to be limiting thereof.

LIST OF REFERENCES 1 device
2 first body
3 second body
4 receptacle
5 control device
6 bulge
7 indentation
8 abutment surface
9 bore
10 coordinate system (XC, YC, ZC)
11a first leg with free end
11b second leg with free end
12 rotational joint
13 raised edge region
S1 point of gravity of first body
S2 point of gravity of second body
X rotational axis

The invention claimed is:

1. A device for supporting a spinal column in the region of the transverse or spinous processions of two adjacent vertebrae and/or for spreading two adjacent ribs, said device comprising:
a first body that defines a first receptacle for receiving a transverse or spinous process of a vertebra or a rib;
a second body that defines a second receptacle for receiving a transverse or spinous process of a vertebra or a rib; and
a rotational joint that connects said first body with said second body such that said first body is rotatable with respect to said second body about a common axis of rotation and such that the separation between said first receptacle and said second receptacle is adjustable according to the rotation of said first body with respect to said second body with said transverse or spinous processes of adjacent vertebrae or adjacent ribs being receivable in said first receptacle and in said second receptacle at times when the angle of rotation between said first body and said second body is in the range of 0° to 180°, the cross-section of said first receptacle of said first body taken transverse to the direction of angular rotation defining a substantially U-shape that has a stop surface between first and second limbs that each have a respective free end, with said first body defining said stop surface of said first receptacle as a surface within said first receptacle that is curved outwardly in the direction of angular rotation, and the cross-section of said second receptacle of said second body taken transverse to the direction of angular rotation defining a substantially U-shape that has a stop surface between first and second limbs that each have a respective free end, with said second body defining said stop surface of said second receptacle as a surface within said second receptacle that is curved outwardly in the direction of angular rotation.

2. The device of claim 1 wherein transverse or spinous processes of adjacent vertebrae or adjacent ribs are receivable in said first receptacle and in said second receptacle at times when the angle of rotation between said first body and said second body is in the range of 0° to 270°.

3. The device according to claim 1 wherein said first receptacle and/or said second receptacle each define a respective concave surface.

4. The device according to claim 3 wherein the respective concave surface of each of said first and second receptacles defines at least a quarter circle.

5. The device according to claim 4 wherein the respective concave surface of each of said first and second receptacles defines at least a semicircle.

6. The device according to claim 1 wherein said rotational joint defines an axis of rotation that is located on said first body oppositely from said first receptacle and/or that is located on said second body oppositely from said second receptacle.

7. The device according to claim 1 further comprising a control device for controlling the rotational movement about said common axis of rotation of said first body with respect to said second body.

8. The device according to claim 7, wherein said control device is integral with said first body and/or is integral with said second body.

9. The device according to claim 1 wherein said rotational joint is a lockable rotational joint whereby said first body can be angularly adjusted with respect to said second body and locked in position with respect to said second body.

10. The device according to claim 9 wherein said first body is angularly adjustable with respect to said second body about said rotational joint by an angle in the range of 0° to 270°.

11. The device according to claim 9 wherein said first body is angularly adjustable with respect to said second body about said rotational joint by an angle in the range of 0° to 180°.

12. The device according to claim 9 wherein said angle between said first body and said second body is adjustable in predefined steps.

13. The device according to claim 12 wherein said first body defines a bulge and said second body defines at least one indentation that cooperates with said bulge so that the bulge engages in said at least one indentation to adjust the angle between the first body and the second body.

14. The device according to claim 12 wherein said first body defines a first bulge and at least one indentation and wherein said second body defines a second bulge and at least one indentation with the bulge of said first body engagable with the at least one indentation of said second body and the bulge of said second body engagable with the at least one indentation of said first body.

15. The device according to claim 1 wherein said first receptacle of said first body includes raised edge regions that guard against slippage of a transverse process or spinous process or a rib from said first receptable and wherein said second receptacle of said second body includes raised edge regions that guard against slippage of a transverse process or spinous process or a rib from said second receptable.

16. The device of claim 1 wherein said first receptacle of said first body and/or said second receptacle of said second body include padding for cushioning transverse or spinous processes or ribs that are accommodated within said first and/or second receptacles.

17. The device according to claim 1 wherein said first receptacle includes a bore for fixing or securing a transverse or spinous process or a rib that is received in said first receptacle and/or wherein said second receptable includes a bore for fixing or securing a transverse or spinous process or a rib that is received in said second receptacle.

18. The device according to claim 1 wherein, at times when the device is arranged for insertion into a human or animal body and before expansion of the dimension between the first and second receptacles by rotational movement of said first body with respect to said second body, the overall dimensions of said device do not exceed 2.5×1.5×1.5 cm.

19. The device according to claim 1 wherein, at times when the device is arranged for insertion into a human or animal body and before expansion of the dimension between the first and second receptacles by rotational movement of said first body with respect to said second body, the overall dimensions of said device do not exceed 2.1×1.1×1.1 cm.

* * * * *